(12) United States Patent
Hwang et al.

(10) Patent No.: US 7,081,258 B2
(45) Date of Patent: Jul. 25, 2006

(54) COMPOSITION FOR PROMOTING HAIR GROWTH

(75) Inventors: Seong-Lok Hwang, Cheongjoo (KR); In-Byeong Yoon, Cheongjoo (KR); Min-Ho Lee, Daejeon (KR); Sug-Youn Chang, Daejeon (KR); Moon-Jeong Rang, Daejeon (KR); Ho-Jeong Ahn, Daejeon (KR)

(73) Assignee: LG Household & Health Care Ltd., Seoul (KR)

( * ) Notice: Subject to any disclaimer, the term of this patent is extended or adjusted under 35 U.S.C. 154(b) by 0 days.

(21) Appl. No.: 10/490,842

(22) PCT Filed: Sep. 28, 2001

(86) PCT No.: PCT/KR01/01642

§ 371 (c)(1),
(2), (4) Date: Oct. 8, 2004

(87) PCT Pub. No.: WO03/041669

PCT Pub. Date: May 22, 2003

(65) Prior Publication Data

US 2005/0053572 A1    Mar. 10, 2005

(51) Int. Cl.
*A61K 35/78* (2006.01)

(52) U.S. Cl. ................... 424/725; 424/728; 424/760

(58) Field of Classification Search ............... 424/725, 424/728, 760
See application file for complete search history.

(56) References Cited

U.S. PATENT DOCUMENTS 6,194,468 B1 * 2/2001 Hattori et al.
6,284,234 B1 * 9/2001 Niemiec et al.

FOREIGN PATENT DOCUMENTS

JP    2000007574 A  *  1/2000
JP    2000080029 A  *  3/2000

* cited by examiner

*Primary Examiner*—Susan D. Coe
(74) *Attorney, Agent, or Firm*—Alston & Bird LLP

(57) ABSTRACT

The present invention relates to a composition for promoting hair growth. More particularly, the present invention comprises a component for inhibiting 5α-reductase activity, a functional component of cell activity, and an expansion component of peripheral blood vessels. A composition for promoting hair growth of the present invention has a superior effect on hair growth.

7 Claims, No Drawings

COMPOSITION FOR PROMOTING HAIR GROWTH

BACKGROUND OF THE INVENTION (a) Field of the Invention

The present invention relates to a composition for promoting hair growth, and particularly to a composition for promoting hair growth comprising an ingredient for inhibiting 5 α-reductase activity, an ingredient for promoting function of cell activity, and an ingredient for dilating peripheral blood vessels.

(b) Description of the Related Art

There are approximately 100,000~150,000 hairs on a human body, and each hair has a different cycle and grows and falls off while passing through anagen, catagen, and telogen phases. Such a cycle is repeated over 3~6 years, and as a result, an average of 50~100 hairs normally fall out per day. Generally, a phenomenon in which the percentage of hairs in the anagen phase decreases and the percentage in the catagen or telogen phases increases, and thus many hairs abnormally fall out, is referred to as "alopecia".

As causes for depilation, excessive function of male hormones, excessive secretion of sebaceous matter, poor blood circulation, scalp function drop due to peroxides, bacteria, etc., genetic factors, aging, stress, etc. have been discussed. Although an exact cause for depilation has not yet been clarified, it is known that very complicated processes are involved therein. Recently, the population suffering from depilation has increased due to increase in stress, by changes in diet, social environments, etc., and the age has lowered and the female depilation population has increased.

As technologies for depilation and hair growth, preparations containing female hormones as main ingredients for promoting blood circulation, reinforcing hair root function, moisturizing the scalp, and inhibiting male hormone function; 5 α-reductase inhibitors; preparations containing minoxidil, trichosaccharides, etc. have been suggested, but they have not shown any marked effects, and side-effect problems are raised.

As technologies for inhibition of depilation and hair growth, preparations containing ingredients for promoting blood circulation, reinforcing hair root function, moisturizing the scalp, etc.; female hormones for inhibiting male hormone function; 5 α-reductase inhibitors; preparations containing minoxidil, trichosaccharides, etc. as main ingredients have been suggested, but they have not shown any marked effects, and side-effect problems are raised.

For example, in order to inhibit 5 α-reductase, a male alopecia-treating agent using finasteride that has been used as a male prostate gland treating agent has been developed, but side effects such as sexual function disorder, etc. have been reported. In addition, Korean Patent Application No. 1998-008238, and Japanese Patent Laid-Publication Nos. 2000-256142, 2000-169497, 2000-095649, 2000-053539, 2000-007534, and 1999-246414 have disclosed 5 α-reductase activity-inhibiting material or compositions using natural extracts such as Sophora flavescens extract, etc. However, hair growth effects are not satisfactory if they are used alone.

The main function of blood circulation is to transfer nutrients or other required materials to tissues, and blood supply is important for hair growth. Shollet and Cotrans have reported that blood vessels around hairs in the anagen phase are more plentiful than those around hairs in the telogen phase, and it is known that as hair papilla becomes larger, the number of micro-blood vessels increases to have a capillary network developed suitably for a large hair follicle. In addition, according to a hypothesis that a scalp flexibility drop or a decrease in peripheral vascular blood flow in subcutaneous scalp cell tissue causes hair growth disorders, if the well-developed capillary network decreases because of primary or secondary factors, the number of hair follicles reduces by a kind of nutrition disorder to manifest clinical depilation symptoms. Minoxidil, known to be a hypertension-treating agent, is widely used to promote hair growth, but it cannot show satisfactory hair growth-promoting effects.

Accordingly, there is a need for development of a hair growth-promoting agent having superior hair growth-promoting effects without side effects.

SUMMARY OF THE INVENTION

In order to solve these problems, it is an object of the present invention to provide a hair growth-promoting agent that does not cause any side effects and has superior hair growth-promoting effects.

In order to achieve these objects, the present invention provides a composition for promoting hair growth comprising a) an ingredient for inhibiting 5 α-reductase activity;

b) an ingredient for promoting cell activity functioning; and c) an ingredient for dilating peripheral blood vessels.

DETAILED DESCRIPTION AND THE PREFERRED EMBODIMENTS

The present invention will now be explained in detail.

The present inventors have studied various causes and process mechanisms for depilation and multilateral mechanisms for promoting hair growth in order to develop a hair growth-promoting agent having superior hair growth-promoting effects. As a result of combining a few hundred ingredients such as male hormone function-controlling ingredients, blood circulation promoting ingredients, cell activity function promoting ingredients, anti-inflammatory ingredients, etc. and screening depilation-preventing and hair growth-promoting effects thereof, they confirmed that hair growth-promoting effects remarkably increase when a 5 α-reductase activity inhibiting ingredient, a cell activity function promoting ingredient, and a peripheral blood vessel dilating ingredient are combined, and completed the present invention.

The hair growth-promoting agent of the present invention comprises a) an ingredient for inhibiting 5 α-reductase activity; b) an ingredient for promoting function of cell activity; and c) an ingredient for dilating peripheral blood vessels.

The ingredient for inhibiting 5 α-reductase activity includes *Sophora flavescens* extract, Coicis semen extract, clove extract, etc., and *Sophora flavescens* extract is particularly preferable. The scientific name of *Sophora flavescens* is *Sophora flavescens* or *Sophora angustifolia*, the herbal medicinal name thereof is Sophorae radix, and its root is used as an herbal medicine. Representative ingredients contained in *Sophora flavescens* include alkaloids such as matrine, oxymatrine, sophoranol, etc.; and flavonoids such as kuraridin, isoanhydroicaritin, etc.; its leaves contain luteolin-7-glucose; and its seed contains cytosine, etc. In addition, *Sophora flavescens* extract is used as a bitter stomachic, a peripheral vascular constrictor, an antipyretic/analgesic, a skin parasiticide, etc., and application of a large dose must be avoided because toxicity appears at 0.4 g/kg or more (Han Daesuk. et. al., Pharmacognosy, Dongmyung Publication, 194–196, 1994).

*Sophora flavescens* extract used in the present invention can be obtained from *Sophora flavescens* by a common extraction method. As an example, it can be prepared by dry-pulverizing purified *Sophora flavescens* to powder, cold-immersing it in an extraction solvent at an amount of approximately 10 times thereof for 5 days, and filtering, concentrating, and lyophilizing the extracted undiluted solution.

An extraction solvent used in the extraction of *Sophora flavescens* is selected from a group consisting of purified water, methanol, ethanol, propanol, butanol, glycerol, propylenegylcol, 1,3-butyleneglycol, methylacetate, ethylacetate, benzene, hexane, diethylether, dichloromethane, and a mixture thereof.

In addition, the *Sophoara flavescens* extract (solid contents) is preferably contained in an amount of 0.0001 to 10 wt % of the total hair growth-promoting agent. If the contents are less than 0.0001 wt %, hair growth effects are insignificant, and if the contents exceed 10 wt %, the effects cannot be proportional to the contents and the desired preparation form cannot be maintained. More preferably, it is contained in an amount of 0.05 to 0.5 wt %.

As the ingredient for promoting function of cell activity, hinokitiol, ginseng extract, red ginseng extract, etc. can be used, and hinokitiol is particularly preferable. The hinokitiol is a crystalline acid material existing in Taiwan hinoki oil, Aomori, Western Red Cedar oil, etc., and it is also named β-thujaplicin and its chemical name is 4-isopropyl-2-hydroxy-cyclohepta-2,4,6-triene-1-on(C10H12O2) or isopropyltropolone. Acidic ingredients are extracted from oil derived from leaves, trunks, and branches of plants pertaining to the Hinoki family *Asnaro* genus, *Kurobe* genus, or *Nezmisashi* genus to obtain raw hinokitiol, and then it is distilled and recrystallized to obtain pure hinokitiol.

According to the present invention, hinokitiol can be extracted from a natural substance or it can be synthesized, and the production method is not specifically limited.

In addition, the hinokitiol is preferably contained in an amount of 0.001 to 1 wt % of the total hair growth-promoting composition. If the contents are less than 0.001 wt %, hair growth effects will be insignificant, and if the contents exceed 10 wt %, the effects will not be proportional to the amount and the desired preparation form cannot be maintained. More preferably, the contents are 0.05 to 0.5 wt %.

As the ingredient for dilating peripheral blood vessels, nicotinamide, benzylnicotinate, Swertia herb extract, etc. can be used, and particularly nicotinamide is preferable. Nicotinamide, a kind of vitamin B complex corresponding to pyridine-3-carboxiamide (C6H6N2O), is also named nicotinamide or niacin amide, it exists as NAD and NADP in living bodies to comprise a co-enzyme, and it is used for peripheral vasodilation and nutrition supply to hair root cells, etc. in cosmetics.

In addition, the nicotinamide is preferably contained in an amount of 0.01 to 10 wt % of total hair growth-promoting composition. If the contents are less than 0.01 wt %, hair growth effects will be insignificant, and if the contents exceed 10 wt %, the effects will not be proportional to the amount and the desired preparation form cannot be maintained. More preferably, the contents are 0.5 wt 2 wt %.

A combination of two or more kinds of each ingredient having effects of a), b), and c) within a range that does not influence stability of preparation form will bring good effects.

In addition, the hair growth-promoting composition of the present invention may further comprise other ingredients mixed with common hair growth-promoting compositions, such as a dandruff preventing agent, an anti-inflammatory, an antibacterial, a keratin softener, a refresher, a moisturizer, etc. together with the ingredients having the effects of a), b), and c). For example, pepper tinct, ginseng extract, red ginseng extract, Coicis Semen extract, Swertia herb extract, clove extract, tocopherol acetate, piroctone olamine, salicylic acid, I-mentol, etc. can be used.

The contents of the additives are not specifically limited if they are within a range that does not disturb the effects of the main ingredients, and that can maintain the preparation form. However, considering safety to a user or stability of the preparation form, the piroctone olamine is preferably contained in an amount of 0.001 to 1.0 wt %; the pepper tinct, ginseng extract, red ginseng extract, Coicis Semen extract, Swertia herb extract, clove extract, tocopherol acetate, etc, are in an amount of 0.001 to 10 wt %; the benzylnicotinate is in an amount of 0.001 to 0.1 wt %; and the salicylic acid, I-mentol, etc. are in an amount of 0.01 to 1.0 wt %.

The hair growth-promoting composition of the present invention can be prepared in all preparation forms that can be applied to the scalp, including liquid, cream, paste, or solid, etc., and it can be prepared for compositions such as shampoo, hair conditioner, hair potion for promoting hair growth, or liquid phase hair growing agent.

As a result of conducting clinical tests on people with alopecia and animal tests using C57BL/6 mice, which are test animals for evaluating hair growth effectiveness, the hair growth-promoting composition of the present invention was found to not cause side effects to a human body, and it shows unexpectedly improved hair growth effects compared to a hair growth-promoting agent containing one or two of a 5 α-reductase activity inhibiting ingredient, a cell activity function promoting ingredient, and a peripheral blood vessel dilating ingredient, as well as an existing hair promoting agent.

The present invention will be explained in more detail with reference to the following Examples, but these are to illustrate the present invention and the present invention is not limited to them.

EXAMPLE

Example 1 and Comparative Examples 1 to 7

A hair growth-promoting composition of Example 1 was prepared with a composition as shown in Table 1 using *Sophora flavescens* as a 5 α-reductase activity-inhibiting ingredient, hinokitiol as a cell activity function promoting ingredient, and nicotinamide as a peripheral blood vessel dilating ingredient. The compositional ratios of the hair growth-promoting compositions of Comparative Examples 1 to 7 are also as shown in Table 1. The ingredient unit is wt % in Table 1.

TABLE 1

|  | Example | Comparative Example | | | | | | |
|---|---|---|---|---|---|---|---|---|
|  |  | 1 | 2 | 3 | 4 | 5 | 6 | 7 |
| Ethanol | 40.0 | 40.0 | 40.0 | 40.0 | 40.0 | 40.0 | 40.0 | 40.0 |
| Sophora Flavescens extract | 0.1 | 0.1 | — | — | 0.1 | 0.1 | — | — |
| Hinokitiol | 0.1 | — | 0.1 | — | 0.1 | — | 0.1 | — |
| Nicotiamide | 1.0 | — | — | 1.0 | — | 1.0 | 0.1 | — |
| Pepper tinct | 0.5 | 0.5 | 0.5 | 0.5 | 0.5 | 0.5 | 0.5 | 0.5 |
| Benzylnicotinate | 0.01 | 0.01 | 0.01 | 0.01 | 0.01 | 0.01 | 0.01 | 0.01 |
| Swertiaherbextract | 0.5 | 0.5 | 0.5 | 0.5 | 0.5 | 0.5 | 0.5 | 0.5 |
| Ginseng extract | 0.5 | 0.5 | 0.5 | 0.5 | 0.5 | 0.5 | 0.5 | 0.5 |
| Coicis semen extract | 0.5 | 0.5 | 0.5 | 0.5 | 0.5 | 0.5 | 0.5 | 0.5 |
| Clove extract | 0.5 | 0.5 | 0.5 | 0.5 | 0.5 | 0.5 | 0.5 | 0.5 |
| Tocopherol acetate | 0.1 | 0.1 | 0.1 | 0.1 | 0.1 | 0.1 | 0.1 | 0.1 |
| Pyroctone olamine | 0.1 | 0.1 | 0.1 | 0.1 | 0.1 | 0.1 | 0.1 | 0.1 |
| Salicylic acid | 0.3 | 0.3 | 0.3 | 0.3 | 0.3 | 0.3 | 0.3 | 0.3 |
| I-mentol | 0.3 | 0.3 | 0.3 | 0.3 | 0.3 | 0.3 | 0.3 | 0.3 |
| Tween 20 | 0.5 | 0.5 | 0.5 | 0.5 | 0.5 | 0.5 | 0.5 | 0.5 |
| Perfume | Appropriate amount | | | | | | | |
| Pigment | Appropriate amount | | | | | | | |
| water | Added to 100 wt % | | | | | | | |

Experiment 1: Animal Test

Hair growth-promoting effects tests were conducted using mice (C57BL/6, male) of age 42~56 days. Hairs around their backs were removed, weights were measured, and they were divided into groups of 10 mice so that body weights were evenly distributed. After an adaptation period of one day, the liquid phase compositions prepared with the compositional ratios as shown in Table 1 were coated on the hair-removed portions. The compositions were coated on the backs in an amount of 100 μl once a day for 40 days per mouse.

The ratio of area where new hairs were grown to area where hairs were removed was measured using a picture analyzer, and the average values were presented in Table 2.

TABLE 2

|  | Example 1 | Comparative Example | | | | | | |
|---|---|---|---|---|---|---|---|---|
|  |  | 1 | 2 | 3 | 4 | 5 | 6 | 7 |
| Area ratio (%) | 92.8 | 48.8 | 44.6 | 41.2 | 58.8 | 52.0 | 51.6 | 28.6 |

As shown in Table 2, the composition of Example 1 showed an area ratio of 92.8%. This result indicates high hair growth effects corresponding to 200% of Comparative Examples 1 to 3 using one of a 5 α-reductase activity inhibiting ingredient, a cell activity function promoting ingredient, and a peripheral blood vessel dilating ingredient, and 170% of Comparative Examples 4 to 6 using 2 kinds of ingredients. This result indicates that when 5-reductase activity inhibition, cell activity function, and peripheral vascular dilation progress together, surprising synergistic effects for hair growth promotion emerge.

Experiment 2: Clinical Test

In order to measure clinical effects for hair growth promotion using the compositions of Example 1 and Comparative Examples 6 and 7, clinical tests were conducted on 10 adult men and women of age 20~50 having alopecia or having an average hair loss of 100 or more hairs per day.

The composition was coated on hair-removed portions by droplet (approximately 2 mL) 2~3 times a day, and it was used for a minimum of 1 month to a maximum of 4 months, according to the degree of effects.

Effects were determined by evaluating average hair loss amount per day at hair washing, examination with the naked eye, and degree of improvement of subjective symptoms according to the standard as shown in Table 3 by 5 grades, and a general improvement degree was set as an average of the evaluation standard.

For the final determination, a composition having a general improvement degree of 3.0 or more was judged to be effective, and the results are as shown in Table 4.

TABLE 3

|  | Hair loss amount at hair washing | Subjective symptoms | Examination with naked eyes |
|---|---|---|---|
| 5 | Remarkable decrease | Remarkable decrease | Remarkable decrease |
| 4 | Serious decrease | Serious decrease | Serious decrease |
| 3 | Slight decrease | Slight decrease | Slight decrease |
| 2 | No change | No change | No change |
| 1 | Aggravation (increase) | Aggravation (increase) | Aggravation (increase) |

TABLE 4

|  | At hair washing | Subjective Symptoms | Examination with the naked eye | General improvement degree |
|---|---|---|---|---|
| Example 1 | 4.3 | 4.1 | 3.8 | 4.1 |
| Comparative Example 6 | 3.0 | 2.9 | 2.8 | 2.9 |
| Comparative Example 7 | 2.5 | 2.6 | 2.3 | 2.5 |

As shown in Table 4, the hair growth-promoting composition of Example 1 of the present invention showed more than serious improvement, indicating that it has remarkably superior hair growth-promoting effects to those of Comparative Example 6 or 7. In addition, no side effects occurred in any subject during the use period, indicating that the composition is safe for the human body.

As explained, the hair growth-promoting composition of the present invention comprising an ingredient for inhibiting 5 α-reductase activity, an ingredient for promoting functioning of cell activity, and an ingredient for dilating peripheral blood vessels has remarkably distinguished effects compared to the existing hair growth-promoting compositions and the hair growth-promoting composition comprising one or 2 kinds of ingredients of a 5 α-reductase activity inhibiting ingredient, a cell activity functioning ingredient, and a peripheral blood vessel dilating ingredient, due to excellent synergism.

What is claimed is:

1. A composition for promoting hair growth, comprising:
   a) *Sophora flavescens* extract;
   b) hinokitiol; and
   c) nicotinamide,
wherein the composition comprises 0.0001 to 10 wt % of the a) *Sophora flavescens* extract on the basis of solid contents of the *Sophora flavescens* extract, 0.001 to 1 wt % of the b) hinokitiol, and 0.01 to 10 wt % of the c) nicotinamide.

2. The composition according to claim 1, further comprising an additive ingredient selected from a group consisting of a dandruff preventing agent, an anti-inflammatory, an antibacterial, a keratin softener, a refresher, a moisturizer, and a mixture thereof.

3. The composition according to claim 1, further comprising an additive ingredient selected from a group consisting of pepper tincture, ginseng extract, red ginseng extract, Coicis semen extract, Swertia herb extract, clove extract, tocopherol acetate, Benzylnicotinate, piroctone olamine, salicylic acid, I-menthol, and a mixture thereof.

4. The composition according to claim 1, comprising about 40.0 wt % ethanol; about 0.1 wt % *Sophora flavescens* extract; about 0.1 wt % hinokitiol; and about 1.0 wt % nicotinamide.

5. The composition according to claim 4, further comprising one or more additional ingredients selected from the group consisting of pepper tincture, benzylnicotinate, Swertia herb extract, ginseng extract, Coicis semen extract, clove extract, tocopherol acetate, piroctone olamine, salicylic acid, 1-menthol, Tween, perfume, pigment, and combinations thereof.

6. The composition according to claim 4, further comprising about 0.5 wt % pepper tincture; about 0.01 wt % benzylnicotinate; about 0.5 wt % Swertia herb extract, about 0.5 wt % ginseng extract; about 0.5 wt % Coicis semen extract, about 0.5 wt % clove extract, about 0.1 wt % tocopherol acetate, about 0.1 wt % piroctone olamine, about 0.3 wt % salicylic acid, and about 0.3 wt % 1-menthol.

7. The composition according to claim 6, further comprising an effective amount of perfume.

* * * * *